(12) United States Patent
Kooistra et al.

(10) Patent No.: US 7,642,363 B2
(45) Date of Patent: *Jan. 5, 2010

(54) PROCESS FOR THE PREPARATION OF 2-(6-SUBSTITUTED-1,3-DIOXANE-4-YL) ACETIC ACID DERIVATIVES

(75) Inventors: Jacob Hermanus Mattheus Hero Kooistra, Venlo (NL); Hubertus Josephus Marie Zeegers, Baarlo (NL); Daniel Mink, Eupen (BE); Joannes Maria Cornelis Antonius Mulders, Geleen (NL)

(73) Assignee: AstraZeneca UK Ltd., London (GB)

( * ) Notice: Subject to any disclaimer, the term of this patent is extended or adjusted under 35 U.S.C. 154(b) by 579 days.

This patent is subject to a terminal disclaimer.

(21) Appl. No.: 11/053,090

(22) Filed: Feb. 7, 2005

(65) Prior Publication Data

US 2005/0148785 A1 Jul. 7, 2005

Related U.S. Application Data

(63) Continuation of application No. 10/333,351, filed as application No. PCT/NL01/00535 on Jul. 12, 2001, now Pat. No. 6,870,059.

(30) Foreign Application Priority Data

Jul. 19, 2000 (NL) .................................. 1015744

(51) Int. Cl.
C07D 309/00 (2006.01)
C07D 319/06 (2006.01)

(52) U.S. Cl. ....................................... 549/273; 549/375

(58) Field of Classification Search .................. 548/252, 548/253; 549/273, 230, 375
See application file for complete search history.

(56) References Cited

U.S. PATENT DOCUMENTS

| | | | |
|---|---|---|---|
| 3,325,466 A | 6/1967 | Anderson | |
| 3,992,432 A | 11/1976 | Napier et al. | 260/465.1 |
| 5,278,313 A | 1/1994 | Thottathil | |
| 5,292,891 A * | 3/1994 | Kaneko et al. | 549/273 |
| 5,294,724 A * | 3/1994 | Jendralla et al. | 549/292 |
| 5,443,970 A | 8/1995 | Blacker et al. | |
| 5,449,793 A * | 9/1995 | Miyazawa et al. | 549/373 |
| 5,457,227 A | 10/1995 | Thottathil | |
| 5,594,153 A | 1/1997 | Thottathil | |
| 6,278,001 B1 | 8/2001 | Solladie et al. | |
| 6,331,641 B1 | 12/2001 | Taoka | |
| 6,340,767 B1 | 1/2002 | Nishiyama | |
| 6,344,569 B1 * | 2/2002 | Mitsuda et al. | 549/375 |
| 6,784,171 B2 | 8/2004 | Taylor et al. | |
| 6,844,437 B1 | 1/2005 | Taylor et al. | |
| 6,870,059 B2 | 3/2005 | Kooistra et al. | |
| 2006/0004200 A1 | 1/2006 | Gudipati et al. | |
| 2006/0040898 A1 | 2/2006 | Puthiaparampil et al. | |

FOREIGN PATENT DOCUMENTS

| | | |
|---|---|---|
| EP | 1024139 | 8/2000 |
| EP | 0 862 646 | 4/2002 |
| GB | 885516 | 12/1961 |
| JP | 4-266879 | 9/1992 |
| JP | 04266879 | 9/1992 |
| WO | WO-91/13876 | 9/1991 |
| WO | WO-93/06235 | 4/1993 |
| WO | WO 93/08823 | 5/1993 |
| WO | WO-96/31615 | 10/1996 |
| WO | WO-97/19185 | 5/1997 |
| WO | WO 97/19917 | 6/1997 |
| WO | WO-99/57109 | 11/1999 |
| WO | WO-00/08011 | 2/2000 |
| WO | WO-00/34264 | 6/2000 |
| WO | WO 00/49014 | 8/2000 |
| WO | WO-00/68221 | 11/2000 |
| WO | WO 01/72706 | 10/2001 |
| WO | WO 01/85975 | 11/2001 |
| WO | WO 02/06266 | 1/2002 |
| WO | WO 03/006439 | 1/2003 |
| WO | WO 03/059901 | 7/2003 |
| WO | WO 03/087112 | 10/2003 |
| WO | WO 03/106447 | 12/2003 |
| WO | WO 2004/014872 | 2/2004 |

(Continued)

OTHER PUBLICATIONS

Harris et al , Acy-CoA:cholestrol o-acyl transferase (ACAT) Inhibitors. J. Med. Chem. 1992, 35, p. 4384-4392.*

(Continued)

Primary Examiner—Taylor Victor Oh
(74) Attorney, Agent, or Firm—Morgan, Lewis & Bockius LLP

(57) ABSTRACT

The invention relates to the preparation of 2-(6-substituted-1,3-dioxane-4-yl)acetic acid derivatives of formula 1, where X stands for a leaving group, and $R_1$, $R_2$, and $R_3$ each independently stand for an alkyl group with 1-3 carbon atoms from 4-hydroxy-6-X-substituted-methyl-tetrahydropyran-2-one compounds, where X is as defined above, with the aid of an acetalization agent, in the presence of an acid catalyst.

The invention also relates to the novel compounds of formula 1 as well as salts and acids to be prepared from these, with the $OR_3$ group in formula 1 being replaced by an OY group, where X, $R_1$ and $R_2$ have the meanings defined above and where Y stands for an alkaline (earth) metal or a substituted or unsubstituted ammonium group or stands for hydrogen, and to the novel compounds of formula 2.

The products concerned are, after conversion into the t-butyl ester of 2-(6-hydroxymethyl-1,3-dioxane-4-yl)acetic acid, important as intermediary products in the preparation of statins.

12 Claims, No Drawings

FOREIGN PATENT DOCUMENTS

| | | |
|---|---|---|
| WO | WO 2004/054986 | 7/2004 |
| WO | WO 2004/103977 | 12/2004 |
| WO | WO 2004/108691 | 12/2004 |
| WO | WO 2004/113314 | 12/2004 |
| WO | WO 2005/023779 | 3/2005 |
| WO | WO 2005/028450 | 3/2005 |
| WO | WO 2005/042522 | 5/2005 |
| WO | WO 2005/063728 | 7/2005 |
| WO | WO 2006/067456 | 6/2006 |

OTHER PUBLICATIONS

Nebergall et al , College Chemistry with qualitative analysis, p. 89,1980.*

Greenberg et al. "Development of an efficient, scalable, aldolase-catalyzed process for enantioselective synthesis of statin intermediates" PNAS 101(16):5788-5793 (2004).

Kaneko et al. "Preparation of optically active 5,6-epoxyhexanoic acid esters as materials for physiologically active substances" Chemical Abstracts+ Indexes, American Chemical Society, Columbus, US 118(11):832 (1993).

March, Advanced Organic Chemistry: Reactions, Mechanisms, and Structure, 4th ed., John Wiley & Sons, Inc, p. 378 (1992).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Morrison and Boyd "Alkaline hydrolysis of esters" Lehrbuch der Organischen Chemie, 2nd ed., Verlag Chemie, p. 739 (1978) (Translation enclosed).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10) :1997-2010 (1993).

Barry et al. (1982) Easy and Efficient Anion Alkylations In Solid-Liquid PTC Conditions, Tetrahedron Lett. 23(51):5407-5408.

Barry et al. (1983) Alkylations En Absence De Solvant Organique. Effets D'Addition D'Oxydes Mineraux Et De Sels D'Ammonium-II, Tetradron 39(16):2673-2677.

Bram et al. (1985) Anionic Activation by Solid-Liquid Phase Transfer Catalysis Without Solvent: An Improvement in Organic Synthesis, Israel J. Chem. 26:291-298.

Halpern (1997) Choosing a Phase-Transfer Catalyst, Phase-Transfer Communications, 3(1):1-16.

Phase Transfer Catalysis, Principles , And Techniques (C.M. Starks; Academic Press, 1978), pp. 140-147.

Chikara et al. (1993) Preparation of optically active 5,6-epoxyhexanoic acid esters as materials for physiologically active substances, Chemical Abstracts+ Indexes, American Chemical Society, vol. 118, No. 11, p. 832, XP002178273.

Gijsen et al. (1996) Recent Advances in the Chemoenzymatic Synthesis of Carbohydrates and Carbohydrate Mimetics, Chem. Rev. 96(1):443-473.

Bennett et al., "Methyl (3R)-3-Hydroxyhex -5-Enoate" Journal of the Chemical Society, Perkin Transactions 1. 1:133-140 (1991).

Chevallet et al., Tetr. Let. 34(46):7409 (1993).

Crowther et al., Org. Synth. 51:96 (1971).

Inanaga et al., Bull. Chem. Soc. Japan 52(7):1989 (1979).

International Search Report mailed on Oct. 9, 2001, for PCT patent application No. PCT/NL01/00535, filed on Jul. 12, 2001, 4 pages.

March, Advanced Organic Chemistry, Reactions, Mechanisms and Structure 1992, p. 392.

Murakami et al., Heterocycles 31(11):2055 (1990).

Murphy and Koehler, J. Org. Chem. (1970) 35(7):2429-2430.

Rayle and Fellmeth, Org Process R&D 3:172 (1999).

Sakaki, "Lipase Catalysed Asymmetric Synthesis of 6-(3-Chloro-2-Hydroxypropyl)-1,3-Dioxin-4-Ones" Tetrahedron: Asymmetry 2(5):343-6 (1991).

Takeda et al., Synthesis p. 1063 (1994).

Thierry et al., Tetr. Let. 39:1557 (1998).

Watanabe et al., Bioorg. & Med. Chem. 5(2):437-444 (1997).

Watanabe et al., Drugs of the Future 24(5):511-513 (1999).

Weiβenfels et al., Z. Chem 12(7):264 (1972).

Ziegler and Berger, Synth. Comm. 9:539-543 (1979).

* cited by examiner

PROCESS FOR THE PREPARATION OF 2-(6-SUBSTITUTED-1,3-DIOXANE-4-YL) ACETIC ACID DERIVATIVES

CROSS-REFERENCE TO RELATED APPLICATION

This application is a continuation of U.S. Ser. No. 10/333,351 filed Jan. 17, 2003, now U.S. Pat. No. 6,870,059 which is a National Stage of PCT/NL01/00535 filed Jul. 12, 2001 and which claims priority of the Netherlands application no. 1015744 filed Jul. 19, 2000. The contents of these applications are incorporated herein by reference.

The invention relates to a process for the preparation of a 2-(6-substituted-1,3-dioxane-4-yl)acetic acid derivative of formula 1

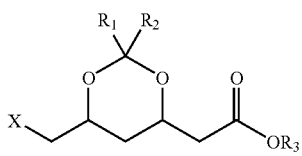

(1)

where X stands for a leaving group, and $R_1$, $R_2$ and $R_3$ each independently stand for an alkyl group with 1-3 carbon atoms, starting from a compound of formula 2

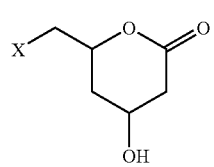

(2)

where X is as defined above, use being made of a suitable acetalization agent, in the presence of an acid catalyst.

The invention also relates to the new compounds of formula 1, as well as salts and acids of formula 3 that can be obtained therefrom

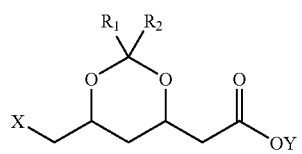

(3)

where $R_1$ and $R_2$ have the above-mentioned meanings and where Y stands for an alkaline (earth)metal or a substituted or non-substituted ammonium group or stands for hydrogen.

Applicant has surprisingly found that the 2-(6-substituted 1,3-dioxane-4-yl)-acetic acid derivative can be obtained selectively and in a high yield from the corresponding compound of formula (2), it being possible to prepare these products, which are relatively little stable, under mild conditions. This is all the more interesting since this provides a simple route via the corresponding salt, the corresponding t-butyl ester, and the 2-hydroxymethyl-substituted compound as intermediates in the preparation of HMG-CoA reductase inhibitors. Optionally the conversion proceeds (depending on the reaction conditions chosen) via an intermediary salt or ester, with the ring in the compound according to formula (2) being opened.

An added advantage of the process according to the invention is that both the starting compounds of formula (2) and the products of formula 3 are found to be crystalline compounds. This is advantageous in obtaining products with a (chemically and stereochemically) high purity. This is important in particular in view of the intended pharmaceutical application. For the intended application in particular the (4R,6S)-2-(6-substituted-1,3-dioxane-4-yl)acetic acid derivative is important. It can be prepared from the corresponding 6-substituted-2,4,6-trideoxy-D-erythrohexose. The invention, therefore, also relates to the starting compounds of formula 1, in particular where X=Cl, and to particles of such compounds. In particular more than 90 wt. % of the particles has a length/diameter ratio between 1:1.5 and 1:6, preferably between 1:2 and 1:4.4 and a length of the particles between 0.05 and 2 mm, in particular between 0.1 and 1 mm. The invention also relates to such particles. The compound of formula II gives clear crystalline particles with a sharp melting point of 73-74° C. The products of formula 3 derived from the (4R,6S)-2-(6-substituted-1,3-dioxane-4-yl)acetic acid derivative of formula 1 can according to the invention be prepared with an enantiomeric excess (e.e.) of more than 95%, in particular more than 99.5%, and with a diastereomeric excess (d.e.) of more than 90%, in particular more than 99.5%.

Examples of suitable leaving groups X that can be applied in the process according to the invention are halogens, in particular Cl, Br or I; tosylate groups; mesylate groups; acyloxy groups, in particular acetoxy and benzoyloxy groups; an aryloxy-, in particular benzyloxy-, or a nitro-substituted benzene sulphonyl group. For practical reasons Cl is preferably chosen as leaving group.

The groups $R_1$, $R_2$ and $R_3$ each separately stand for an alkyl group with 1-3 carbon atoms, preferably methyl or ethyl. In practice $R_1=R_2=R_3=$methyl is most preferred.

Examples of suitable acetalization agents that can be applied in the process according to the invention are dialkoxypropane compounds, with the alkoxy groups each preferably having 1-3 carbon atoms, for instance 2,2-dimethoxypropane or 2,2-diethoxypropane; alkoxypropene, with the alkoxy group preferably having 1-3 carbon atoms, for instance 2-methoxypropene or 2-ethoxypropene. Most preferred is 2,2-dimethoxypropane. This can optionally be formed in situ from acetone and methanol, preferably with water being removed.

As acid catalyst use can be made of the acid catalysts known for acetalization reactions, preferably non-nucleophilic strong acids, for example sulphonic acids, in particular p-toluene sulphonic acid, methane sulphonic acid of camphor sulphonic acid; inorganic acids with a non-nucleophilic anion, for example sulphuric acid, phosphoric acid: acid ion exchangers, for example DOWEX; or solid acids, for example the so-called heteropolyacids.

The acetalization can be carried out without using a separate solvent; if desired the reaction can also be carried out in an organic solvent. Examples of suitable organic solvents are ketones, in particular acetone, hydrocarbons, in particular aromatic hydrocarbons, for example toluene, chlorinated hydrocarbons, for example methylene chloride.

The temperature at which the acetalization reaction is carried out preferably lies between −20° C. and 60° C., in particular between 0° C. and 30° C. The acetalization reaction is preferably carried out under an inert atmosphere.

The molar ratio of acetalization agent to starting compound of formula (2) preferably lies between 1:1 and 20:1, in particular between 3:1 and 5:1. Using an organic solvent the molar ratio is in particular between 1:1 and 2:1.

The molar ratio of acid catalyst to starting compound of formula (2) preferably lies between 1:1 and 0.001:1, in particular between 0.01:1 and 0.05:1.

The resulting 2-(6-substituted-1,3-dioxane-4-yl)acetic acid derivative can subsequently be hydrolyzed in the presence of a base and water to form the corresponding salt of formula 3

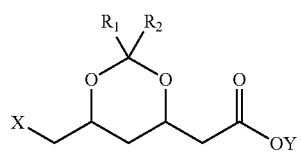

(3)

where Y stands for an alkaline metal, an alkaline earth metal, or a substituted or unsubstituted ammonium group, preferably Na, Ca or a tetraalkyl-ammonium compound. Optionally; the hydrolysis is followed by conversion to the acetic acid according to formula 3 with Y=H.

The hydrolysis of the compound of formula (3) is preferably carried out with at least 1 base equivalent, in particular 1-1.5 base equivalents, relative to the compound of formula (3). In principle a larger excess can be used, but in practice this usually does not offer any advantages.

The reaction is preferably carried out at a temperature between −20° C. and 60° C., in particular between 0° C. and 30° C.

The hydrolysis can for example be carried out in water, an organic solvent, for example an alcohol, in particular methanol or ethanol, an aromatic hydrocarbon, for example toluene, or a ketone, in particular acetone or methyl isobutyl ketone (MIBK), or a mixture of an organic solvent and water, optionally catalysed by a phase transfer catalyst (PTC) or addition of a cosolvent.

The hydrolysis can also be carried out enzymatically, the desired diastereomer optionally being hydrolyzed selectively.

Examples of enzymes that can suitably be used in the process according to the invention are enzymes with lipase or esterase activity, for example enzymes from *Pseudomonas*, in particular *Pseudomonas fluorescens, Pseudomonas fragi; Burkholderia*, for example *Burkholderia cepacia; Chromobacterium*, in particular *Chromobacterium viscosum; Bacillus*, in particular *Bacillus thermocatenulatus, Bacillus licheniformis; Alcaligenes*, in particular *Alcaligenes faecalis; Aspergillus*, in particular *Aspergillus niger, Candida*, in particular *Candida antarctica, Candida rugosa, Candida lipolytica, Candida cylindracea; Geotrichum*, in particular *Geotrichum candidum; Humicola*, in particular *Humicola lanuginosa; Penicillium*, in particular *Penicillium cyclopium, Penicillium roquefortii, Penicillium camembertii; Rhizomucor*, in particular *Rhizomucor javanicus, Rhizomucor miehei; Mucor*, in particular *Mucor javanicus; Rhizopus*, in particular *Rhizopus oryzae, Rhizopus arhizus, Rhizopus delemar, Rhizopus niveus, Rhizopus japonicus, Rhizopus javanicus*; porcine pancreas lipase, wheat germ lipase, bovine pancreas lipase, pig liver esterase. Preferably, use is made of an enzyme from *Pseudomonas cepacia, Pseudomonas* sp., *Burkholderia cepacia*, porcine pancreas, *Rhizomucor miehei, Humicola lanuginosa, Candida rugosa* or *Candida antarctica* or subtilisin. If an enantioselective enzyme is used, even further enantiomer enrichment is realized during the hydrolysis. Such enzymes can be obtained using commonly known technologies. Many enzymes are produced on a technical scale and are commercially available.

The salts (acids) obtained are novel. The invention therefore also relates to these products of formula 3

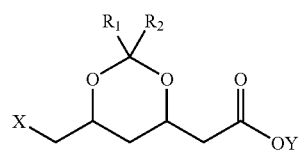

(3)

where X stands for a halogen, in particular Cl, Br or I, a tosylate or mesylate group, an acyloxy group with 3-10 carbon atoms, or a nitro-substituted benzene sulphonyl group and Y stands for H, an alkaline (earth) metal, or a substituted or unsubstituted ammonium group.

The resulting salt of formula 3 can subsequently be converted into the corresponding t-butyl ester (formula 1a with $R_3$=t-butyl), in a way known per se.

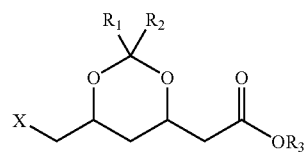

(1a)

In the process according to the invention the compound of formula (3) can for example be esterified to form the corresponding tert. butyl ester using the following methods, which in general are described in literature:

reaction with isobutene and strong acid, for example para-toluene sulphonic acid (pTS), sulphuric acid or a strongly acidic ion exchanger (U.S. Pat. No. 3,325,466);

reaction via the acid chloride and t-butanol, under the influence of a base, for example triethylamine ($Et_3N$), dimethylamino pyridine (DMAP). The acid chloride can be prepared with the aid of for example $SOCl_2$, $POCl_3$, $(COCl)_2$ and catalyzed by for example dimethyl formamide (DMF) (J. Org. Chem. 35 2429 (1970));

reaction via the acid chloride with Li-t-butanolate (Org. Synth. 51 96 (1971));

transesterification with t-butyl acetate under the influence of a strong acid (Z. Chem. 12(7) 264 (1972));

reaction of the salt with t-butyl bromide, preferably in DMF, dimethyl acetamide (DMAA), 1-methyl-2-pyrrolidinone(NMP) and using a phase transfer catalyst (PTC) (Tetr. Let. 34 (46) 7409 (1993));

reaction of the acid with t-butanol, 1,3-dicyclohexyl carbodiimide (DCC) and DMAP (Synth. Comm. 9, 542 (1979));

reaction of the acid with t-butyl-trichloro acetamidate (Tetr. Let. 39, 1557 (1998));

reaction of the salt with carboxyl diimidazole (CDI) and t-butanol;

reaction of the acid with pivaloyl chloride and t-butanol under the influence of DMAP or N-methyl-morpholin (NMM) (Bull. Chem. Soc. Japan 52 (7) 1989 (1979));

reaction of the salt with di-tert. butyl dicarbonate, DMAP and t-butanol (Synthesis 1063 (1994));

reaction of the acid with cyanuric chloride and pyridine or triethylamine (Org Process R&D 3, 172 (1999); Heterocycles 31 11, 2055 (1990)).

The resulting t-butyl ester of 2-(6-substituted-1,3-dioxane-4-yl)acetic acid can subsequently be converted into the 2-(6-hydroxymethyl-1,3-dioxane-4-yl)acetic acid, for example as described in U.S. Pat. No. 5,594,153 or in EP-A-1024139, in the presence of a tetraalkyl ammonium halogenide and/or a carboxylic acid in the salt, via conversion into a compound of formula 1a with $R_3$=t-butyl and X=an acyloxy, for example an acetoxy group. The acyloxy group can subsequently be converted via solvolysis, in a way otherwise generally known, to a hydroxyl group. The solvolysis can be performed using a base ($Na_2CO_3$, $K_2CO_3$, or sodium methanolate in methanol), optionally by simultaneous distillation of the methyl acetate formed.

The t-butyl ester of 2-(6-hydroxymethyl-1,3-dioxane-4-yl) acetic acid is a desirable intermediate product in the preparation of various statins, for example ZD-4522, as described in Drugs of the future, (1999), 24(5), 511-513 by M. Watanabe et al., Bioorg. & Med. Chem. (1997), 5(2), 437-444. The invention therefore provides a novel, interesting route to these intermediate products and to the end products, in particular statins.

The starting compounds of formula 2 can for example be obtained as described in WO-A-96/31615.

The invention will be elucidated with reference to the following examples, without however being restricted by these.

EXAMPLE I

Preparation of (4R,6S)-4-hydroxy-6-chloromethyl-tetrahydropyran-2-one (Compound II; Covered by Formula 2)

At room temperature 2.1 ml bromine was added in 45 minutes to a mixture of 6.7 g (40 mmol) 6-chloro-2,4,6-trideoxy-D-erythro-hexose (compound I; prepared according to the method described in WO-A-96/31615) and 6.7 g sodium bicarbonate in 40 ml methylene chloride and 10 ml water. $CO_2$ gas escaped, while the pH remained at 5. After stirring for one hour, according to gas-liquid chromatography (GLC) the starting material had been fully converted. The bromine excess was neutralized with solid $Na_2S_2O_3$. After phase separation the water phase was extracted with 2 times 100 ml ethyl acetate. The combined organic phases were dried over $Na_2SO_4$ and filtered. After rotavap evaporation 5.5 g yellow oil was obtained (82% yield of the compound of formula (2) with X=Cl relative to compound I).

$^1$H NMR (200 MHz, $CDCl_3$): δ 1.8-2.1 (m, 2H); 2.6-2.7 (m, 2H); 3.5-3.8 (m, 2H($CH_2Cl$)); 4.4 (m, 1H); 4.9 (m, 1H).

EXAMPLE II

Preparation of (4R,6S)-4-hydroxy-6-chloromethyl-tetrahydropyran-2-one (Compound II; Covered by Formula 2)

To a solution of 75 g (450 mmole) compound I in 390 ml water was added 114 g (715 mmole) of bromine at 15-25° C. in 3 hours. The pH of the reaction mixture was maintained at 5-6 via the simultaneous addition of sodium carbonate (88 g total amount). The excess of bromine was neutralized with sodium bisulfite. The product was extracted from the water phase with ethyl acetate (counter-current extraction).

The product was crystallized from ethyl acetate/heptane (125 g/62 g). After cooling to 0° C., the crystals were filtered, washed with 50 ml of heptane/ethyl acetate (w:w=9:1) and dried, yielding 49.2 g (67% relative to compound I) of compound II as colourless needles (m.p. 73-74° C.).

EXAMPLE III

Preparation of (4R-cis)-6-(chloromethyl)-2,2-dimethyl-1,3-dioxane-4-yl acetic acid methyl ester (Compound III)

5.5 g of compound II as obtained in example I was added to 20 ml commercial dimethoxy propane and 100 mg p-toluene sulphonic acid monohydrate at room temperature. After stirring for one hour at room temperature GLC analysis showed that full conversion had taken place and a clear solution had been formed. After addition of 500 mg $NaHCO_3$ stirring took place for 30 minutes at room temperature. After filtration and rotavap evaporation 7.1 g compound III was obtained as a light-yellow oil (91% relative to compound II).

$^1$H NMR (200 MHz, $CDCl_3$): δ 1.25 (dt, 1H); 1.40 (s, 3H); 1.47 (s, 3H); 1.79 (dt, 1H); 2.42 (dd, 1H); 2.58 (dd, 1H); 3.40 (dd, 1H); 3.52 (dd, 1H); 3.70 (s, 3H); 4.1 (m, 1H); 4.35 (m, 1H).

EXAMPLE IV

Preparation of (4R-cis)-6-(chloromethyl)-2,2-dimethyl-1,3-dioxane-4-yl acetic acid methyl ester (Compound III)

To a solution of 49.2 g (300 mmole) of compound II in 100 ml of toluene was added 47 g (450 mmole) dimethoxy propane and 850 mg p-toluene sulphonic acid monohydrate (4.5 mmole).

After stirring for one hour at room temperature, GLC analysis showed complete conversion of compound II.

The toluene phase was washed with 50 ml of a 0.2N NaOH solution in water. After evaporation 67 g of compound III was obtained as a light-yellow oil (94% relative to compound II).

EXAMPLE V (4R-cis)-(6-chloromethyl)-2,2-dimethyl-1,3-dioxane-4-yl-acetic acid, sodium salt (Compound IV)

55 g (233 mmol) of compound III was added to 200 ml water. At room temperature 20 g of a 50% NaOH solution in water was added dropwise in 2 hours at pH=12. The hydrolysis was monitored using GLC. After 20 g the pH remained constant. Concentrated hydrochloric acid was used to lower the pH to 10. The water phase was washed with 100 ml ethyl acetate and evaporated using a rotavap. The oil formed was dried by stripping with absolute ethanol and toluene. The solid was stirred into 200 ml acetone, filtered and washed with cold acetone. Yield after vacuum drying: 45.6 g=80% Na salt relative to compound III.

$^1$H NMR (200 MHz, $CDCl_3/CD_3OD$): δ 1.21 (dt, 1H); 1.36 (s, 3H); 1.49 (s, 3H); 1.79 (dt, 1H); 2.25 (dd, 1H); 2.45 (dd, 1H); 3.46 (m, 2H); 4.11 (m, 1H); 4.36 (m, 1H).

EXAMPLE VI (4R-cis)-(6-chloromethyl)-2,2-dimethyl-1,3-dioxane-4-yl-acetic acid, sodium salt (Compound IV)

Starting from 49.2 g compound I, a solution of compound III in toluene was prepared as described in example IV.

5 g methanol and 25 ml of water were added. At room temperature 25 g of a 50% solution of NaOH in water was added dropwise in 1 hour.

After stirring for 4 hours at room temperature, GLC analysis indicated complete hydrolysis.

The excess of base was neutralized to pH 8.5-9.5 with 33% HCl solution in water. The waterphase was separated and dried via azeotropic distillation using 470 ml of toluene, yielding 65 g compound IV as a 16 w/w % suspension in toluene with KF<0.1%.

The suspension can be used for the synthesis of compound V.

EXAMPLE VII (4R-cis)-(6-chloromethyl)-2,2 dimethyl-1,3-dioxane-4-yl-acetic acid, t-butyl ester (Compound V)

45.5 g IV, sodium salt (186 mmol) was added to a solution of 159 g ditert. butyl dicarbonate in 1400 ml dry tert. butanol. After addition of 6.8 g dimethylamino pyridine stirring took place for 16 hours at 40° C. The reaction mixture was poured out into 1500 ml ethyl acetate and 1000 ml saturated ammonium chloride. The water phase was re-extracted with 1500 ml ethyl acetate. The combined organic phases were washed with 600 ml saturated NaCl solution. The organic layer was dried over $Na_2SO_4$, filtered and then evaporated under vacuum, yielding 51.9 g yellow oil (100% relative to compound IV).

$^1$H NMR (200 MHz, $CDCl_3$): δ 1.15-1.33 (m, 1H); 1.40 (s, 3H); 1.45 (s, 3H); 1.47 (s, 9H) 1.77 (dt, 1H); 2.33 (dd, 1H); 2.46 (dd, 1H); 3.40 (dd, 1H); 3.49 (dd, 1H) 4.08 (m, 1H); 4.28 (m, 1H).

EXAMPLE VIII (4R-cis)-6-[(acetoxy)methyl]-2,2-dimethyl-1,3-dioxane-4-yl-acetic acid, t-butyl ester (Compound VI)

Starting from 33 g of compound V obtained according to example VII, in 16 hours 29 g of compound VI was obtained at 100° C. according to U.S. Pat. No. 5,457,227 (using 40 g tetra-n-butyl ammonium acetate and in 200 ml DMF), as a solid after crystallization from 75 ml heptane.

$^1$H NMR (200 MHz, $CDCl_3$): δ 1.1-1.3 (dt, 1H); 1.39 (s, 3H); 1.45 (s, 9H); 1.47 (s, 3H); 1.57 (dt, 1H); 2.08 (s, 3H); 2.32 (dd, 1H); 2.46 (dd, 1H); 4.0-4.2 (m, 3H); 4.3 (m, 1H).

EXAMPLE IX (4R-cis)-6-[hydroxymethyl]-2,2-dimethyl-1,3-dioxane-4-yl-acetic acid, t-butyl ester (Compound VII)

Starting from 29 g of compound VI according to example V, 25.0 g compound VII was obtained as a light-yellow oil with e.e.=100%, d.e.=99.9% (according to GLC) according to U.S. Pat. No. 5,457,227 (use being made of 6.9 g potassium carbonate in 300 ml methanol).

$^1$H NMR (200 MHz, $CDCl_3$): Spectrum was in line with literature (Synthesis 1014, 1995).

The invention claimed is:

1. A compound of formula (3),

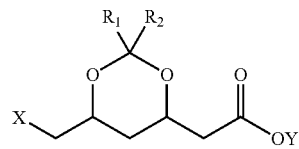

wherein
each $R_1$ and $R_2$ is independently an alkyl group with 1-3 carbon atoms;
Y is an alkaline metal, an alkaline earth metal, or a tetraalkyl-substituted or unsubstituted ammonium group; and
X is a tosylate group, a mesylate group, an acyloxy group, an aryloxy-substituted benzene sulfonyl group or a nitro-substituted benzene sulfonyl group, wherein the acyloxy group has 3-10 carbon atoms.

2. The compound of claim 1, wherein Y is Na, Ca or tetraalkyl ammonium.

3. The compound of claim 1, wherein said compound is in the 4R,6S form.

4. The compound of claim 3, wherein said compound has an enantiomeric excess of more than 90%.

5. The compound of claim 4, wherein said compound has an enantiomeric excess of more than 99%.

6. The compound of claim 1, wherein each $R_1$ and $R_2$ is independently methyl.

7. A compound of formula (1),

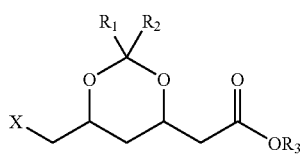

wherein
each $R_1$, $R_2$ and $R_3$ is independently an alkyl group with 1-3 carbon atoms; and
X is acyloxy, a tosylate group, an aryloxy-substituted benzene sulfonyl group or a nitro-substituted benzene sulfonyl group.

8. A compound having formula (2) in the (4R,6S) form,

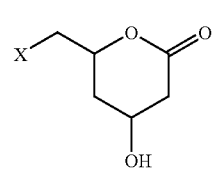

where X is a tosylate group, a mesylate group, an acyloxy group, an aryloxy-substituted benzene sulfonyl group, or a nitro-substituted benzene sulfonyl group.

9. The compound of claim 8, wherein the compound exists as particles having a particle length/diameter ratio between 1:1.5 and 1:6.

10. The compound of claim 8, wherein the compound exists as particles having a particle length between 0.05 and 2 mm.

11. The compound of claim 8, wherein the compound exists as particles having a particle length between 0.1 and 1 mm.

12. The compound of claim 8, wherein said acyloxy group has 3-10 carbons.

* * * * *